United States Patent
Singh

(10) Patent No.: US 7,706,883 B1
(45) Date of Patent: Apr. 27, 2010

(54) EFFICIENT DATA RETRIEVAL FOR IMPLANTABLE MEDICAL DEVICES

(75) Inventor: Tejpal Singh, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 1022 days.

(21) Appl. No.: 11/400,810

(22) Filed: Apr. 6, 2006

(51) Int. Cl.
*A61N 1/08* (2006.01)

(52) U.S. Cl. .............................. 607/27; 607/59; 607/60

(58) Field of Classification Search ............. 607/59–60, 607/27
See application file for complete search history.

(56) References Cited

U.S. PATENT DOCUMENTS 5,843,134 A * 12/1998 Thong et al. .................. 607/17

2003/0204146 A1 * 10/2003 Carlson ........................ 600/515

FOREIGN PATENT DOCUMENTS

WO    WO 03/092494 A1    11/2003

* cited by examiner

*Primary Examiner*—Mark W Bockelman
*Assistant Examiner*—Eric D. Bertram

(57) ABSTRACT

Techniques for communicating with implantable medical devices (IMDs) in a manner that promotes efficient data retrieval are described. The techniques involve ways to streamline retrieval of data stored on a patient's IMD. In one exemplary technique, first and second data ranges are determined for retrieval from an IMD. The technique evaluates whether the first data range overlaps or is separated by less than a predefined amount from the second data range. In an event where the first and second data ranges overlap or are separated by less than the predefined amount, the technique requests a third data range from the IMD which encompasses the first and second data ranges.

13 Claims, 6 Drawing Sheets

EFFICIENT DATA RETRIEVAL FOR IMPLANTABLE MEDICAL DEVICES

TECHNICAL FIELD

The present invention generally relates to implantable medical devices and retrieving data from such implantable medical devices.

BACKGROUND

Implantable medical devices (IMDs) continue to be integrated into various aspects of patient care. For instance, IMDs are utilized to sense patient conditions and/or deliver therapy(s) to the patient. IMDs are employed with various organ systems, such as the neurological system, endocrine system, and circulatory system, among others. In relation to the circulatory system, IMDs are in widespread use. IMDs, such as pacemakers and defibrillators, monitor many different cardiac parameters that may be used to determine how well a patient's heart is functioning. For instance, IMDs can measure morphology-related parameters, impedance, intrinsic heart rate, heart rate recovery, heart rate variability, conduction delay, pressure, posture, activity, and so forth. This patient data can be used to evaluate the patient's heart, overall patient health and/or to deliver appropriate therapy to the patient.

IMDs are commonly configured to stimulate the heart with pulses in response to analysis of individual measured parameters, or combinations of the measured parameters. Additionally, the IMDs can store these measured parameters over time and periodically communicate them to external computing device(s) for further analysis. In some scenarios, one communication session might involve interrogating the IMD to retrieve the patient data, analyzing the patient data, and reprogramming a functionality of the IMD based upon the analyzed patient data. During some sessions, this process of interrogating, analyzing, and reprogramming may be repeated for multiple iterations in an attempt to address a patient condition. Efficient communication between an IMD and an external computing device is therefore desired, promoting several advantages. For instance, in some cases, the patient's health may depend upon timely data transfer within a communication session. Where the IMD is reprogrammed based upon the patient data, for example, efficient data transmission may influence a life or death outcome. In a more subtle scenario, a patient's quality of life may be enhanced when communication sessions between the IMD and the external computing device can be accomplished in a timely manner so that the patient can return to other pursuits.

SUMMARY

Techniques for communicating with implantable medical devices (IMDs) in a manner that promotes efficient data retrieval are described. The techniques involve ways to read buffers on the IMD to streamline retrieval of data stored in the buffers. In one exemplary technique, first and second electrogram target buffer addresses are obtained from an implantable medical device (IMD) of a patient. A first buffer address range is calculated for the first electrogram target buffer address and a second buffer address range is calculated for the second electrogram target buffer address. The first and second buffer address ranges are analyzed to detect overlap. If the ranges overlap, a read command for a third buffer address range that encompasses the first and second buffer address ranges is formulated and employed. This eliminates redundant reading of the overlapping ranges, thereby improving the efficiency of the data retrieval.

In another exemplary technique, first and second data ranges are determined for retrieval from an IMD. The technique evaluates whether the first data range overlaps or is separated by less than a predefined amount from the second data range. In an event where the first and second data ranges overlap or are separated by less than the predefined amount, the technique requests a third data range from the IMD which encompasses the first and second data ranges.

DETAILED DESCRIPTION

Overview

Figure 1:
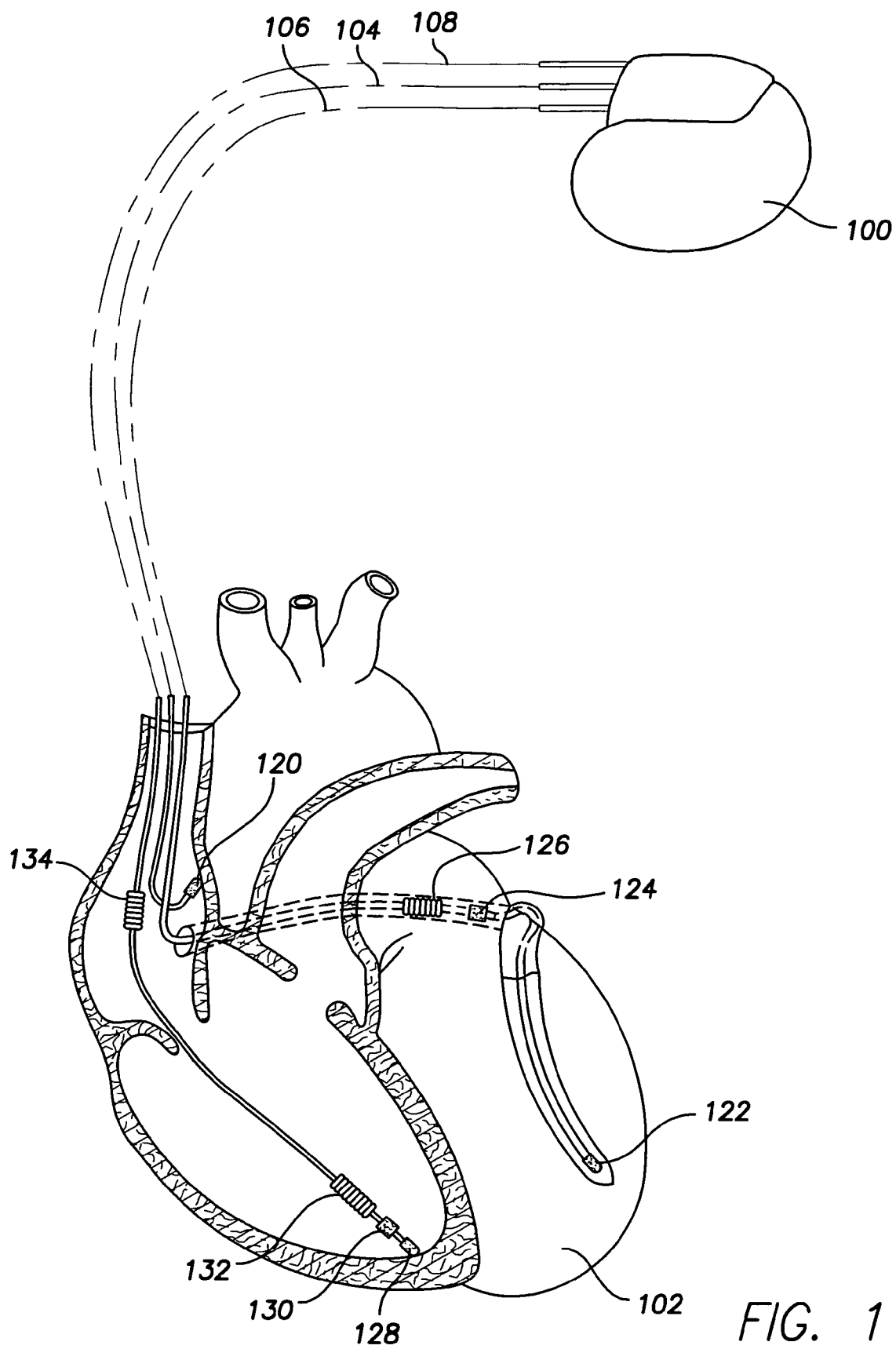
FIG. 1 illustrates an implantable medical device in electrical communication with a patient's heart for multi-chamber sensing and delivery of multi-chamber stimulation and shock therapy.

The following discussion describes techniques for communicating with implantable medical devices (IMDs) in a way that promotes efficient data retrieval. These IMDs are implanted in a patient to gather patient data and/or to treat a patient condition. For instance, an implantable cardiac device (ICD) may be utilized to sense cardiac-related data, such as thoracic impedance data, or intracardiac electrogram data, among others. Intracardiac electrogram data is graphical data relating to cardiac electrical signals sensed from within the patient, such as by an ICD. More generally, IMDs may be used to sense electrogram data, which is graphical data taken from the measurement of events in living tissues.

A computing device, such as a programmer, external to the patient communicates with the IMD and retrieves the parameters and other data sensed and stored by the IMD. The programmer may then analyze or otherwise process the patient data retrieved from the IMD. Communications between the IMD and the programmer are accomplished via a communication mechanism, such as a wireless mechanism which has a finite transfer rate.

In some scenarios, the IMD may be programmed to identify specific types of events within the patient data. These events are referred to hereinafter as "target events". A target event can be any event that may be of interest in evaluating the patient. For instance, a target event may be a change in blood pressure. In another example, a target event may be specific configurations or occurrences of a patient's electrogram. The IMD senses and stores patient data and may also identify the target events. The IMD may map or otherwise reference a location of individual target events within the stored patient data for ease of locating the target events.

The programmer may interrogate the IMD to obtain the target events. The programmer may be configured to retrieve a given amount of patient data surrounding individual target events to provide context for the target event. This patient data surrounding a target event is known as a data range. The programmer can obtain the data range from the IMD during an interrogation process by sending a data request, such as a read command, to the IMD for the data range.

A majority of communication sessions between the IMD and the programmer do not involve a single target event and associated data range, but instead involve a plurality of target events and associated data ranges. As such, time and/or resources may be saved by evaluating a set of target events before requesting associated data ranges. These data ranges may even overlap in some situations. Hence, prior to retrieving all of the data ranges, some processing is performed to define an optimized data range that captures the data for the various events without duplicity. Such implementations reduce redundant transmission and/or processing of patient data during a communication session. Reducing redundant data transmissions can, among other advantages, positively affect patient health and/or quality of life. For instance, session times can be shortened and/or patient treatment can be updated more quickly by reducing redundant data requests and/or transmissions.

Further, some of the present implementations detect data ranges, which while not overlapping, are separated by an amount of data which is less than a predefined value. In such instances a single data request encompassing the data ranges can utilize reduced processing resources and/or be obtained faster than separate individual data requests. Exemplary implementations are described in more detail below in a cardiac context, but such implementations are equally applicable to other IMD scenarios.

Exemplary Implantable Cardiac System

FIG. 1 shows an exemplary implantable medical device (IMD) 100 embodied as an implantable cardiac device (e.g., ICD, pacemaker) in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the IMD 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables IMD 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
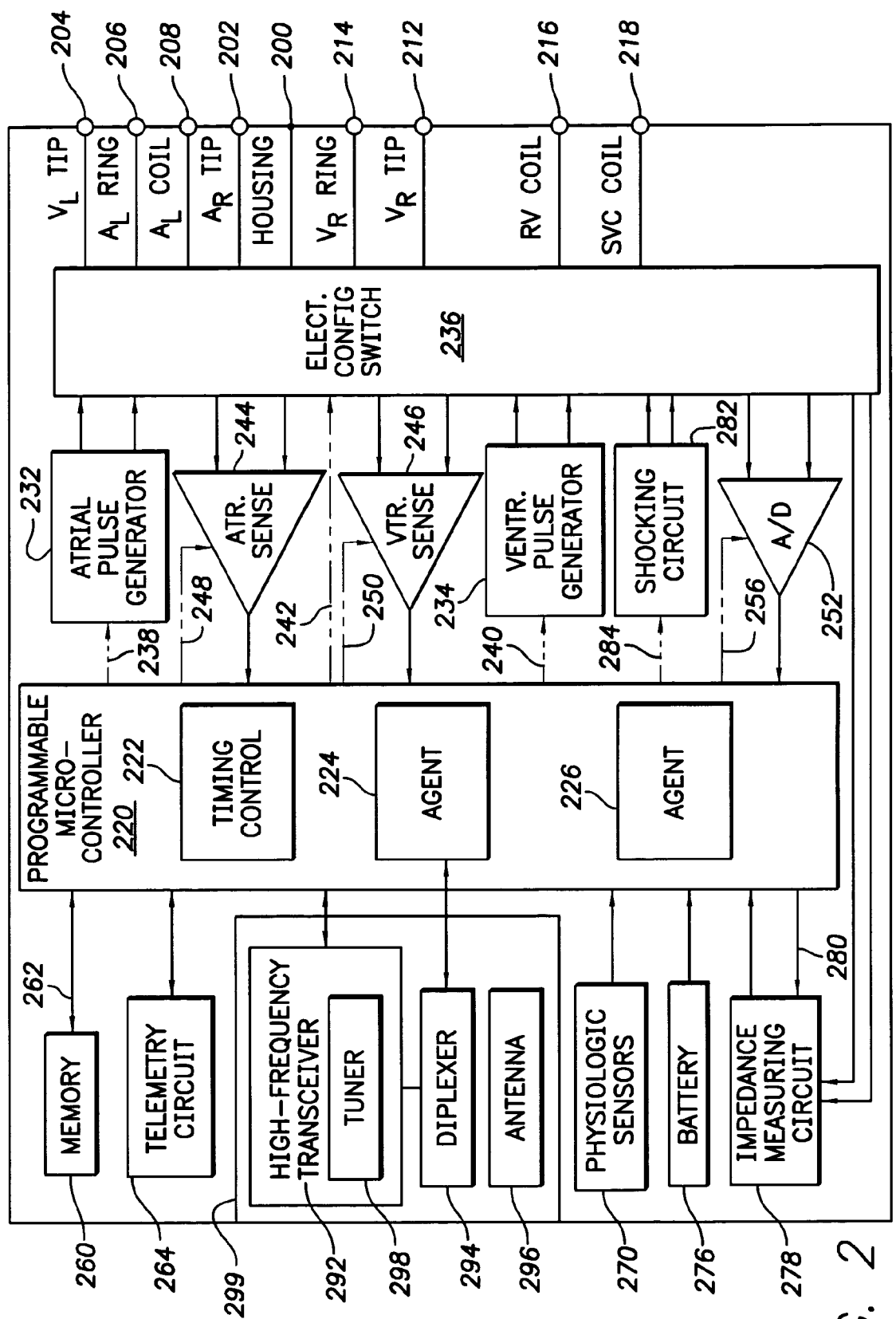
FIG. 2 illustrates a functional block diagram of the multi-chamber implantable medical device.

FIG. 2 shows an exemplary, simplified block diagram depicting various components of IMD 100. The IMD 100 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

Various circuitry is housed in a housing 200, which is often referred to as the "can", "case", "encasing", or "case electrode", and may be programmably selected to act as a return electrode for unipolar modes. Housing 200 may further be used as a return electrode alone or in combination with one or more of the coil electrodes for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. To support right chamber sensing, pacing, and shocking, the connector includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the IMD 100 is a programmable microcontroller 220 that controls various operations of the IMD, including cardiac monitoring and stimulation therapy. Microcontroller 220 includes a microprocessor (or equivalent control circuitry), RAM and/or ROM memory, logic and timing circuitry, state machine circuitry, and I/O circuitry. Microcontroller 220 includes the ability to process or monitor input signals (data) as controlled by a program code stored in a designated block of memory. Any suitable microcontroller 220 may be used.

For discussion purposes, microcontroller 220 is illustrated as including timing control circuitry 222 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and so on. Microcontroller 220 may further include a plurality of agents 224, 226. The agents, when executed, can be utilized to effectuate functionality of the IMD 100. The agents 224, 226 may be implemented in hardware as part of the microcontroller 220, or as software/firmware instructions programmed into the device and executed on the microcontroller 220 during certain modes of operation. In one such example of agent functionality, an agent may be utilized to identify target events in sensed data gathered by the IMD's physiological sensors (which are described below). The agent can map or otherwise reference a location where individual events are stored within the IMD's memory (which is described below).

The IMD 100 further includes an atrial pulse generator 232 and a ventricular pulse generator 234 that generate pacing stimulation pulses for delivery by the right atrial lead 104, the coronary sinus lead 106, and/or the right ventricular lead 108 via an electrode configuration switch 236. It is understood that in order to provide stimulation therapy in each of the four chambers of the heart, the atrial and ventricular pulse generators, 232 and 234, may include dedicated, independent pulse generators, multiplexed pulse generators, or shared pulse generators. The pulse generators 232 and 234 are controlled by the microcontroller 220 via appropriate control signals 238 and 240, respectively, to trigger or inhibit the stimulation pulses.

The electronic configuration switch 236 includes a plurality of switches for connecting the desired electrodes to the appropriate I/O circuits, thereby providing complete electrode programmability. Accordingly, switch 236, in response to a control signal 242 from the microcontroller 220, determines the polarity of the stimulation pulses (e.g., unipolar, bipolar, combipolar, etc.) by selectively closing the appropriate combination of switches (not shown).

Atrial sensing circuits 244 and ventricular sensing circuits 246 may also be selectively coupled to the right atrial lead 104, coronary sinus lead 106, and the right ventricular lead 108, through the switch 236 to detect the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Each sensing circuit 244 and 246 may further employ one or more low power, precision amplifiers with programmable gain and/or automatic gain control, bandpass filtering, and a threshold detection circuit to selectively sense the cardiac signal of interest. The automatic gain control enables the IMD 100 to deal effectively with the difficult problem of sensing the low amplitude signal characteristics of atrial or ventricular fibrillation. Switch 236 determines the "sensing polarity" of the cardiac signal by selectively closing the appropriate switches. In this way, the clinician may program the sensing polarity independent of the stimulation polarity.

The outputs of the atrial and ventricular sensing circuits 244 and 246 are connected to the microcontroller 220 which, in turn, is able to trigger or inhibit the atrial and ventricular pulse generators 232 and 234, respectively, in a demand fashion in response to the absence or presence of cardiac activity in the appropriate chambers of the heart. The sensing circuits 244 and 246 receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits 244 and 246.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device (examples of which are described below in relation to FIG. 3. The data acquisition system 252 is coupled to the right atrial lead 104, the coronary sinus lead 106, and the right ventricular lead 108 through the switch 236 to sample cardiac signals across any pair of desired electrodes.

The data acquisition system 252 may be coupled to the microcontroller 220, or other detection circuitry, to detect an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 234 to generate a stimulation pulse, starting a capture detection window using the timing control circuitry 222 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. The operating parameters may be updated through communication with an external device, such as an IMD manager or programmer described below in relation to FIG. 3. With memory 260, the IMD 100 is able to sense and store a relatively large amount of data (e.g., from the data acquisition system 252) at specific addresses in memory 260. The microcontroller may further, identify specific target events from the patient data and store the addresses where the specific target addresses are stored in memory. IMD 100 may subsequently transmit some or all of the data to the external computing device(s) for subsequent analysis.

Operating parameters of the IMD 100 may be non-invasively programmed into the memory 260 through a telemetry circuit 264 in telemetric communication with an external device, such as a programmer (described below in relation to FIGS. 3-4). The telemetry circuit 264 advantageously allows patient data such as electrogram data, buffer addresses relating to electrogram data, and status information relating to the operation of the IMD 102 (as contained in the microcontroller 220 or memory 260) to be sent to the external devices.

The IMD 100 can further include one or more physiologic sensors 270, commonly referred to as "rate-responsive" sensors because they are typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states, detecting position or postural changes, etc.). Accordingly, the microcontroller 220 responds by adjusting the various pacing parameters (such as rate, AV Delay, V-V Delay, etc.) at which the atrial and ventricular pulse generators, 232 and 234, generate stimulation pulses. While shown as being included within the IMD 100, it is to be understood that the physiologic sensor 270 may also be external to IMD 100, yet still be implanted within or carried by the patient. Examples of physiologic sensors that may be implemented in IMD 100 include known sensors that, for example, sense respiration rate and/or minute ventilation, pH of blood, ventricular gradient, and so forth.

The IMD 100 additionally includes a battery 276 that provides operating power to all of circuits shown in FIG. 2. If the IMD 100 is configured to deliver pacing or shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. As one example, the IMD 100 employs lithium/silver vanadium oxide batteries.

The IMD 100 can further include magnet detection circuitry (not shown), coupled to the microcontroller 220, to detect when a magnet is placed over the IMD. A magnet may be used by a clinician to perform various test functions of the IMD 100 and/or to signal the microcontroller 220 that the external programmer is in place to receive or transmit data to the microcontroller 220 through the telemetry circuits 264.

The IMD 100 further includes an impedance measuring circuit 278 that is enabled by the microcontroller 220 via a control signal 280. Uses for the impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 236 so that any desired electrode may be used.

In the case where the IMD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a voltage delivery circuit or shock circuit 282 by way of a control signal 284. The shocking circuit 282 generates shocking pulses of low (up to 0.5 Joules), moderate (0.5-10 Joules), or high energy (11 to 40 Joules), as controlled by the microcontroller 220. Such shocking pulses are applied to the patient's heart through at least two shocking electrodes, and as shown in this implementation, selected from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The IMD 100 is further designed with the ability to support high-frequency wireless communication, typically in the radio frequency (RF) range. The IMD 100 is equipped with a high-frequency transceiver 292 and a diplexer 294. High-frequency signals received by a dedicated antenna 296, or via leads 104, 106, and 108, are passed to the transceiver 292 directly, or via diplexer 294. The high-frequency transceiver 292 may be configured to operate on one or a few frequencies. Alternatively, the transceiver 292 may include a tuner 298 that tunes to various frequencies when attempting to establish communication links with the external communication device (e.g., IMD manager, programmer, local transceiver, etc.).

In one implementation, the high-frequency circuitry may be contained within a secondary, isolated casing 299 to enable handling of high-frequency signals in isolation from the cardiac therapy circuitry. In this manner, the high-frequency signals can be safely received and transmitted, thereby improving telemetry communication, without adversely disrupting operation of the other device circuitry.

Exemplary IMD Management System

Figure 3:
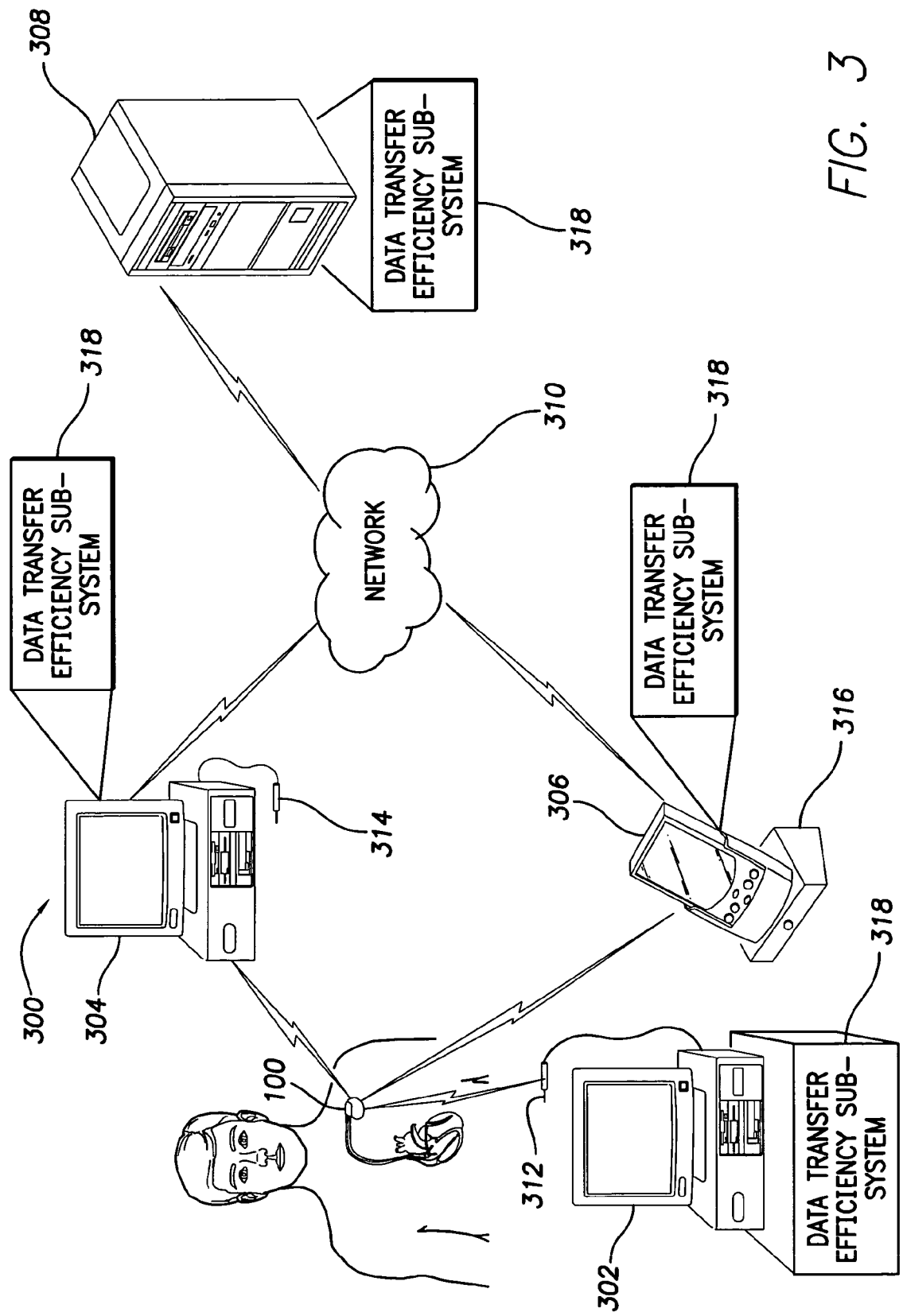
FIG. 3 illustrates a diagnostic system where communication can occur between an implantable medical device and one or more external computing devices.

FIG. 3 shows an IMD management system 300 that includes the IMD 100 and one or more external computing devices that are capable of communicating with the IMD. The external computing devices may be implemented as a programmer, an IMD manager, or other type of computing device. For example, FIG. 3 illustrates a programmer 302 in a standalone configuration, a programmer 304 in a networked configuration, and an IMD manager 306 in a networked configuration. Networked programmer 304 and networked IMD manager 306 communicate with a remote computing sub-system 308 over a network 310. In a stand alone configuration, such as is represented by programmer 302, processing of IMD data is handled by the programmer. In a networked configuration, some or all processing of IMD data may be handled by remote computing sub-system 308.

Communication between IMD 100 and the external computing device(s) can be achieved by various mechanisms. For instance, in this illustration, IMD 100 communicates with standalone or offline programmer 302 via short-range telemetry technology. The standalone programmer 302 is equipped with a wand 312 that, when positioned proximal to IMD 100, communicates with the IMD 100 through a magnetic coupling. Similarly, networked programmer 304 has a wand 314 for communicating with IMD 100.

In an alternative configuration, IMD manager 306 can function as a local transceiver that is intended to be located near the patient. IMD manager 306 may be configured as an electronic communication device that is worn by the patient or is situated proximal to the patient, such as on a structure within the room or residence of the patient. IMD manager 306 communicates with the IMD 100 using short-range telemetry or longer-range high-frequency-based telemetry, such as RF (radio frequency) transmissions.

Networked programmer 304 and IMD manager 306 communicate with other external computing devices directly or via a network. In the illustrated implementation, IMD manager 306 transmits patient data received from IMD 100 to remote computing sub-system 308 when docked in a docking station or base unit 316 which is connected to network 310. The networked programmer 304 is similar in operation to standalone programmer 302, but differs in that it has a network port for connection to the network 310. Remote computing sub-system 308 includes one or more computers for processing and storing data from IMD 100.

The network 310 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 310 can be configured to support any number of different protocols, including HTTP (HyperText Transport Protocol), TCP/IP (Transmission Control Protocol/Internet Protocol), WAP (Wireless Application Protocol), Bluetooth, and so on.

The external computing devices 302-306 are equipped with a data transfer efficiency sub-system 318 to request data associated with target events in an efficient manner. Further, in a network configuration, remote computing sub-system 308 may alternatively or additionally be equipped with a data transfer efficiency sub-system 318. During a communication session with IMD 100, an external computing device may receive target events from the IMD as part of an interrogation process. In some scenarios, the interrogation process may retrieve target events which have accumulated in the IMD over a period of days or weeks before interrogation by the external computing device. In another scenario, the IMD may be identifying multiple target events from sensed data in real-time and be involved in ongoing communications with the external computing device during a communication session. One such scenario might occur when a patient experiences a myocardial infraction in a clinical setting. In this scenario, patient data may be sensed by the IMD, target events identified, and patient data retrieved by the external device as quickly as possible.

In many instances, a range of data before and after a target event can prove useful in analyzing patient health. For instance, in relation to an electrogram target event, data preceding the target event may indicate conditions which led to the target event. Data following the target event may indicate an outcome following the target event. For instance, did the heart return to a normal rhythm or continue in an abnormal condition. In many cases, there are prescribed ranges for different types of events that are standardized in the industry. Data ranges associated with target events can be requested from the IMD during a communication session. Data transfer efficiency sub-system 318 can determine if data requests to the IMD can be formulated which efficiently utilize data transfer resources associated with the communication session. An exemplary data transfer efficiency sub-system 318 is described in more detail below in relation to programmer 302.

Exemplary Programmer

Figure 4:
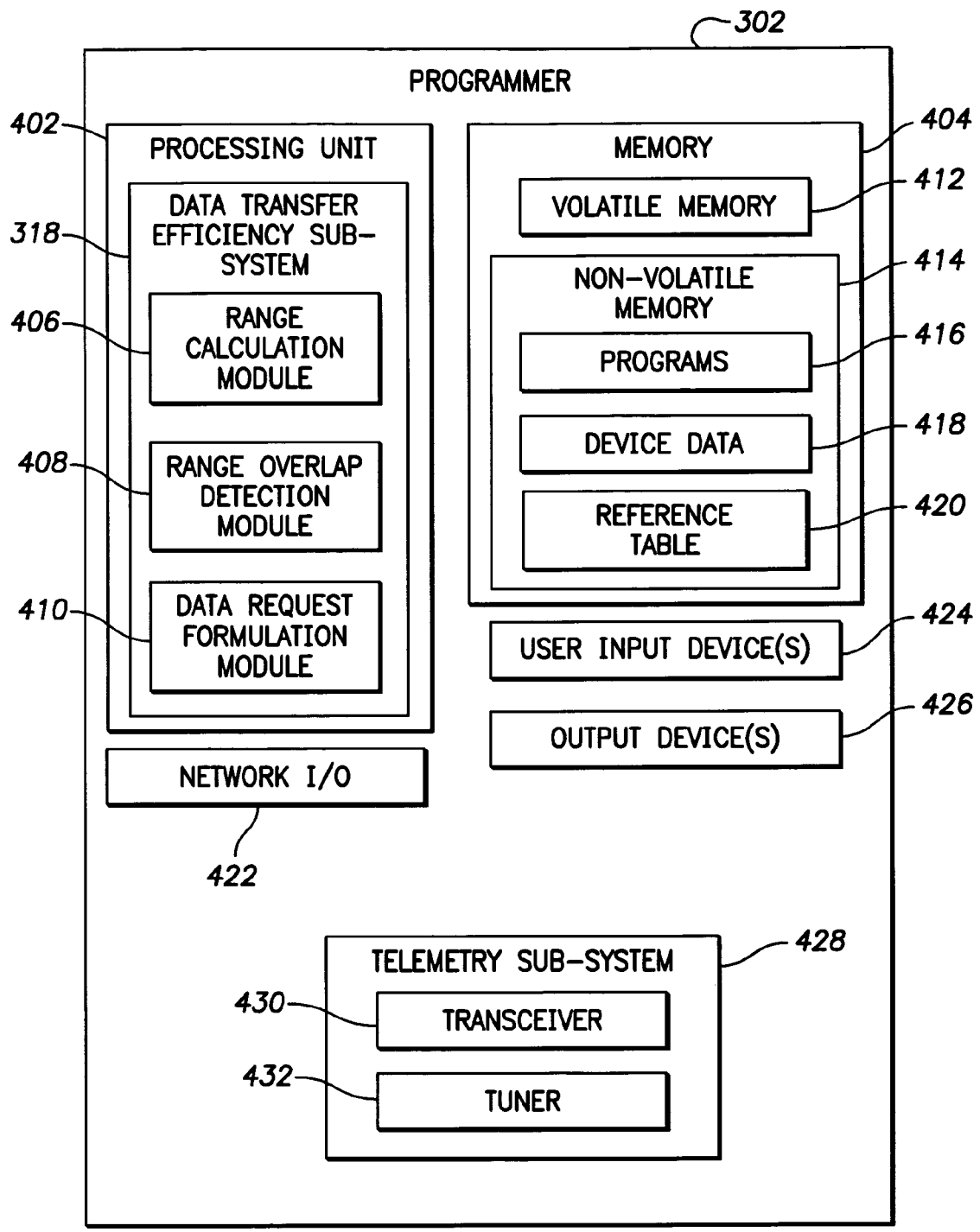
FIG. 4 illustrates a functional block diagram of an external computing device in the form of a programmer.

FIG. 4 shows a component diagram of exemplary programmer 302 described above in relation to FIG. 3. Programmer 302 includes a processing unit 402 and memory 404. The processing unit 402 controls operations carried out by the programmer 302, such as programming an implantable medical device (IMD), gathering data from the IMD, and/or carrying out various testing or diagnostic functions. In this particular configuration, processing unit 402 includes a data transfer efficiency sub-system 318. In this example the data transfer efficiency sub-system includes a range calculation module 406, a range overlap detection module 408, and a data request formulation module 410.

Memory 404 includes both volatile memory 412 (e.g., RAM) and non-volatile memory 414 (e.g., ROM, EEPROM, Flash, disk, optical discs, persistent storage, etc.). Programs, operating parameters, and algorithms 416 that are used in controlling the programming and testing functions may be stored in memory 404. When a program is running, various instructions are loaded into volatile memory 412 and executed by processing unit 402. Device data 418 collected from the IMD may be stored in the programmer's memory 404 for subsequent analysis and/or transfer to external computing devices. Memory 404 also may include various pre-established values such as in the form of reference tables 420 which may be utilized by the processing unit 402. Examples of how reference tables 420 are utilized by the data transfer efficiency sub-system 318 are described below.

The programmer's processing unit 402 is configured to obtain a set of target events during a communication session with an IMD. The range calculation module 406 is configured to determine a desired data range for individual target events. For instance, the range calculation module 406 accesses a reference table 420 in memory 404. The reference table indicates a pre-established duration or amount of data to obtain before and after a target event. In some instances, different types of target events may have different durations associated with them. For instance, for electrogram data, the reference table may specify for atrial target events a range of 100 milliseconds of data to be obtained before the event and 750 milliseconds to be obtained after the event. For ventricular type events, the reference table may specify, for instance, 400 milliseconds of data before the target event and 450 milliseconds after the target event. These examples are provided for purposes of explanation and are not intended to be critical or limiting in any way and other examples may have data ranges of different overall duration and/or starting and ending durations. Still further, other target event types may be referenced for an amount of data before and after a target event rather than a duration of data.

Range overlap detection module 408 is configured to detect whether the data ranges calculated for the various target events overlap. In one implementation the range overlap detection module 408 organizes the data ranges chronologically or by ascending memory addresses to determine whether a first data range begins or ends within a second data range.

Data request formulation module 410 is configured to formulate a single data request, such as a read command for the IMD which encompasses the overlapping data ranges. Examples of such instances are described in more detail below in relation to FIGS. 5-6.

In some implementations, the range overlap detection module 408 is further configured to detect incidences where data ranges, while not overlapping, are separated by less than a predefined amount or duration of patient data in the IMD's memory. For example, in one system configuration, simply making a read command may utilize a given amount of data transfer resources between the IMD 100 and the programmer 302. For purposes of explanation, assume that this given amount of data has a hypothetical value of '10 processing resource units'. This hypothetical predefined value may be stored in reference table 420 for access by data request formulation module 410. If two data ranges are separated by an amount of data corresponding to less than 10 processing resource units then the data request formulation module 410 may formulate a single data request that encompasses the two data ranges. Such an example is provided below in relation to FIG. 6.

The programmer 302 may further be equipped with a network I/O connection 422 to facilitate communication with network 310 (designated in relation to FIG. 3). The network I/O 422 may be a wire-based connection (e.g., network card, modem, etc.) or a wireless connection (e.g., RF transceiver, Bluetooth device, etc.).

The programmer 302 may also include one or more user input device(s) 424 (e.g., keyboard, mouse, stylus, touch pad, touch screen, voice recognition system, etc.) and one or more output device(s) 426 (e.g., monitor, LCD, speaker, printer, dedicated storage systems, etc.).

The programmer 302 is equipped with a telemetry sub-system 428 to communicate with an implantable medical device. The telemetry sub-system 428 may include a transceiver 430 and/or tuner 432.

The components illustrated in FIG. 4 are interconnected via one or more buses (not shown). Additionally, various aspects of the methods and systems described throughout this disclosure may be implemented in computer software or firmware as computer-executable instructions. When executed, these instructions direct the programmer (alone, or in concert with other programmers) to perform various functions and tasks described herein.

Exemplary Processes/Techniques

Figure 5:
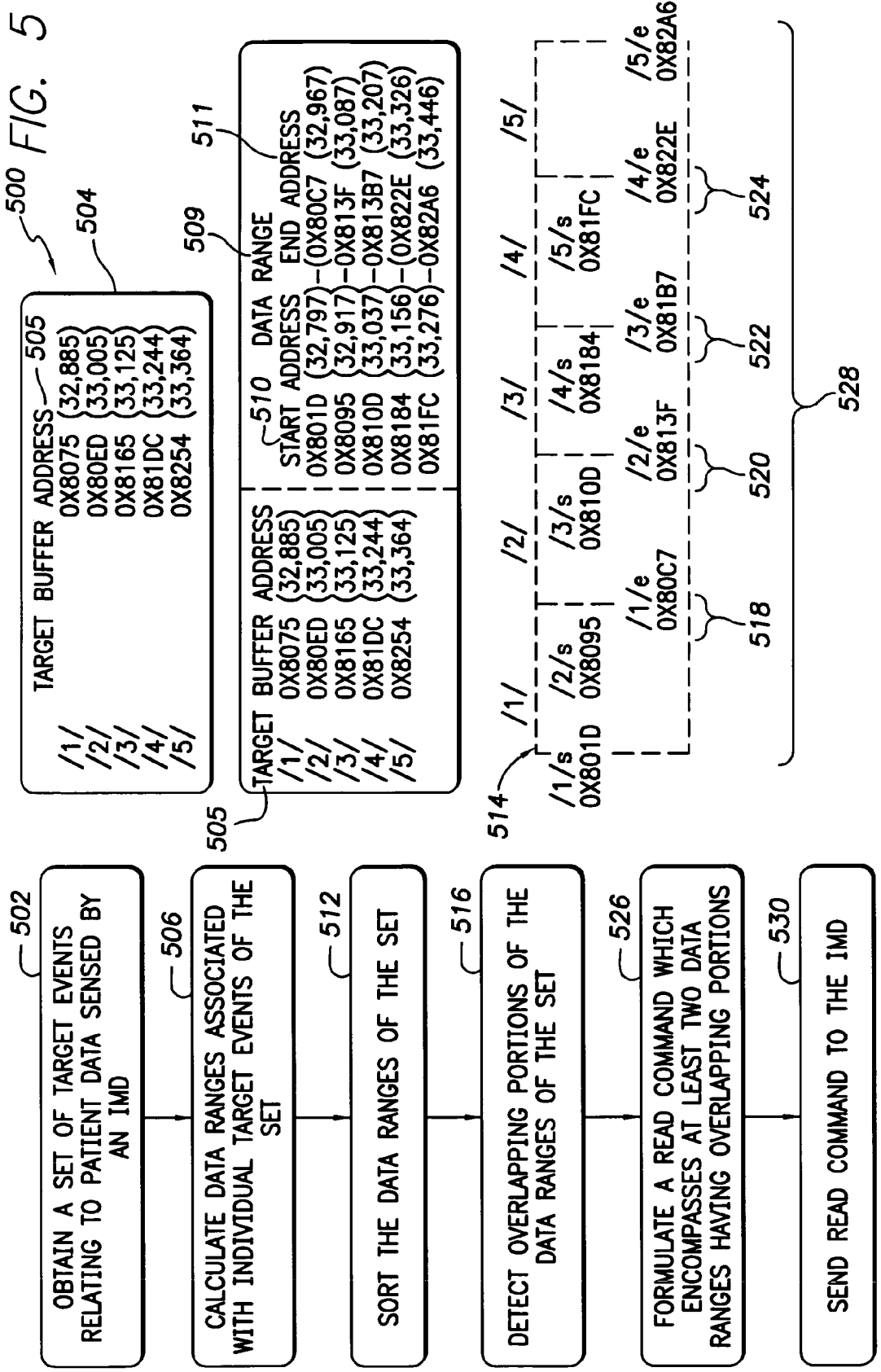
FIG. 5 is a flow diagram of an exemplary implantable medical device communication process accompanied by graphical examples for formulating a data request in accordance with one exemplary technique.

FIG. 5 illustrates one exemplary process implementation for efficient IMD data transfer requests. FIG. 5 illustrates the exemplary process 500 in the form of process blocks on the left side of the physical page upon which FIG. 5 appears. On the right side of the physical page, FIG. 5 further illustrates example buffer addresses that help explain the operations presented in the process blocks. In process 500, operations are summarized in individual blocks. The operations may be performed in hardware and/or as machine-readable instructions (software or firmware) that can be executed by a processor, such as processing unit 402 at programmers 302 and 304.

At block 502, a set of target events relating to patient data sensed by an IMD is obtained. For instance, the set of target events may be obtained by an external computing device (e.g., programmer 302 or 304) during interrogation of the IMD during a communication session. In the example of programmer 302, the programmer's processing unit obtains the target events via the telemetry sub-system and stores the target events in memory.

An example set of target events 504 is indicated generally in a table form. In this instance, the target events are conveyed as target buffer addresses 505 which indicate where the target events are buffered in the IMDs memory. This particular example is provided in the context of electrogram data sensed and stored by an IMD. Other scenarios involving other types of sensed data and associated target addresses should be recognized by the skilled artisan. In this example, the set of target events 504 includes five individual hexadecimal buffer addresses 0x8075, 0x80ed, 0x8165, 0x81dc, and 0x8254 (corresponding decimal values are provided in parenthesis for purposes of explanation). Individual target values are listed on rows designated /1/-/5/within the table. The row designators are carried through the discussion of FIG. 5 with their respective target buffer addresses for ease of explanation.

At block 506, the process 500 calculates data ranges associated with individual target events of the set. The data ranges can have any desired amount of data before and/or after the target event. For instance, one process may be set up to study one second's worth of data on each side of the target event. Other processes may have different specifications for different types of target events. In the cardiac arena, an atrial target event of an electrogram may have pre-established specifications for an amount of data to be obtained before and after the target event and different pre-established specifications for target ventricular events. The data ranges may be calculated, for example, by the range calculation module 406 (FIG. 4).

An example of data ranges associated with individual target events is illustrated generally at 508 in a table form. The left side of table 508 lists the individual target buffer addresses 505. The right side of table 508 lists respective data ranges 509 for individual target buffer addresses 505. In this example, the data ranges 509 are described by a start address 510 and an end address 511 for an individual data range 509 corresponding to an individual target buffer address 505. As evidenced by table 508, each data range 509 has a start address 510 which precedes the target buffer address 505 by about 88 bytes and an end address 511 for the data range 509 which follows the target buffer address by about 70 bytes. Stated another way, to calculate a data range for a particular target event in this example, the process 500 subtracts a pre-established amount (88 bytes) from the target event address to calculate a starting point of the data range and adds a pre-established amount (70 bytes) to the target event address to calculate the ending point of the data range. As mentioned above, there is no criticality associated with the pre-established amounts used in this example to calculate the data range start and end values 510, 511.

At block 512, the data ranges of the set are sorted. Various techniques may be employed for sorting the data ranges. Such techniques may, for example, sort the data ranges by byte address or chronological value among others.

An example of sorted data ranges is indicated graphically on chart 514 where the data ranges are sorted numerically with buffer address values increasing from left to right on the printed page of FIG. 5. Target buffer address /1/appears on the far left of chart 514 and target buffer address /5/appears on the right side with the remaining target buffer addresses interposed therebetween.

At block 516, the process 500 detects any overlapping portions of the data ranges of the set. For instance, the process may compare starting and ending address of the data ranges to determine whether a start address or end address of a first data range falls between start and end addresses of a second data range. Several such examples are designated in relation to chart 514. For example, designator 518 indicates an instance where a start address (designated as /2/s) of the second data range begins within the first data range defined by starting address /1/s and ending address /1/e. Further examples are evidenced at designators 520, 522, and 524. The sorting and overlap detection operations of process blocks 512 and 516 may be performed, for example, by the programmer's range overlap detection module 408 of programmer 302 (FIG. 4).

At block 526, the process formulates a read command which encompasses at least two data ranges having overlapping portions. One such read command is designated graphically at 528 and has a data range of 0x801d (32,797)-0x82a6 (33,446) which encompasses the data ranges /1/-/5/. In this particular instance, the start address of read command 528 is defined by the start address of the first data range which is overlapped by another data range. So in this example, the start address of the first data range (/1/s) defines the start address of read command 528. Similarly, the end address of read command 528 is defined by the end address of the last consecutively overlapping data range which in this instance is the end of data range /5/e. As one example, the programmer's data request formulation module 410 is configured to accomplish the functionality of formulating the read command in block 526.

Stated another way, block 526 entails a merge operation where addresses of multiple data ranges are merged into a single read command. The merging operation can offer significant data transfer reductions. Consider for instance the illustrated example, which involves five data ranges /1/-/5/ each of which includes 171 bytes. Utilizing traditional techniques five separate data requests are generated which cause 5×171 or 855 bytes of data to be transferred. Contrastingly, the read command designated at 528 obtains the same desired data, but only encompasses transferring 650 bytes of data. The 650 bytes is calculated by subtracting the start address /1/s 0x801d (32,797) of the first data range from the end address /5/e of 0x82a6 (33,446) of the last data range. In this example, 255 fewer bytes of data are transferred utilizing the present implementations than would otherwise be the case. In this instance, the savings is related, at least in part, to reducing duplicative requests for the same data.

At block 530, the read command is sent to the IMD. As one example, the programmer's telemetry sub-system 428 is configured to accomplish the functionality of sending the read command of block 530. This process block facilitates reading the buffer corresponding to the read command. So for instance, buffered data corresponding to the read command can be sent by the IMD to an external computing device responsive to the read command. The external computing device, such as a programmer, receives and processes the data corresponding to the read command. The receiving and processing may be accomplished by a single device, such as a programmer, or some or all of the processing may be accomplished by a different device, such as a remote computing sub-system. In one such case described above in relation to FIG. 3, the processing is accomplished by a system including programmer 304 networked to remote computing sub-system 308.

Figure 6:
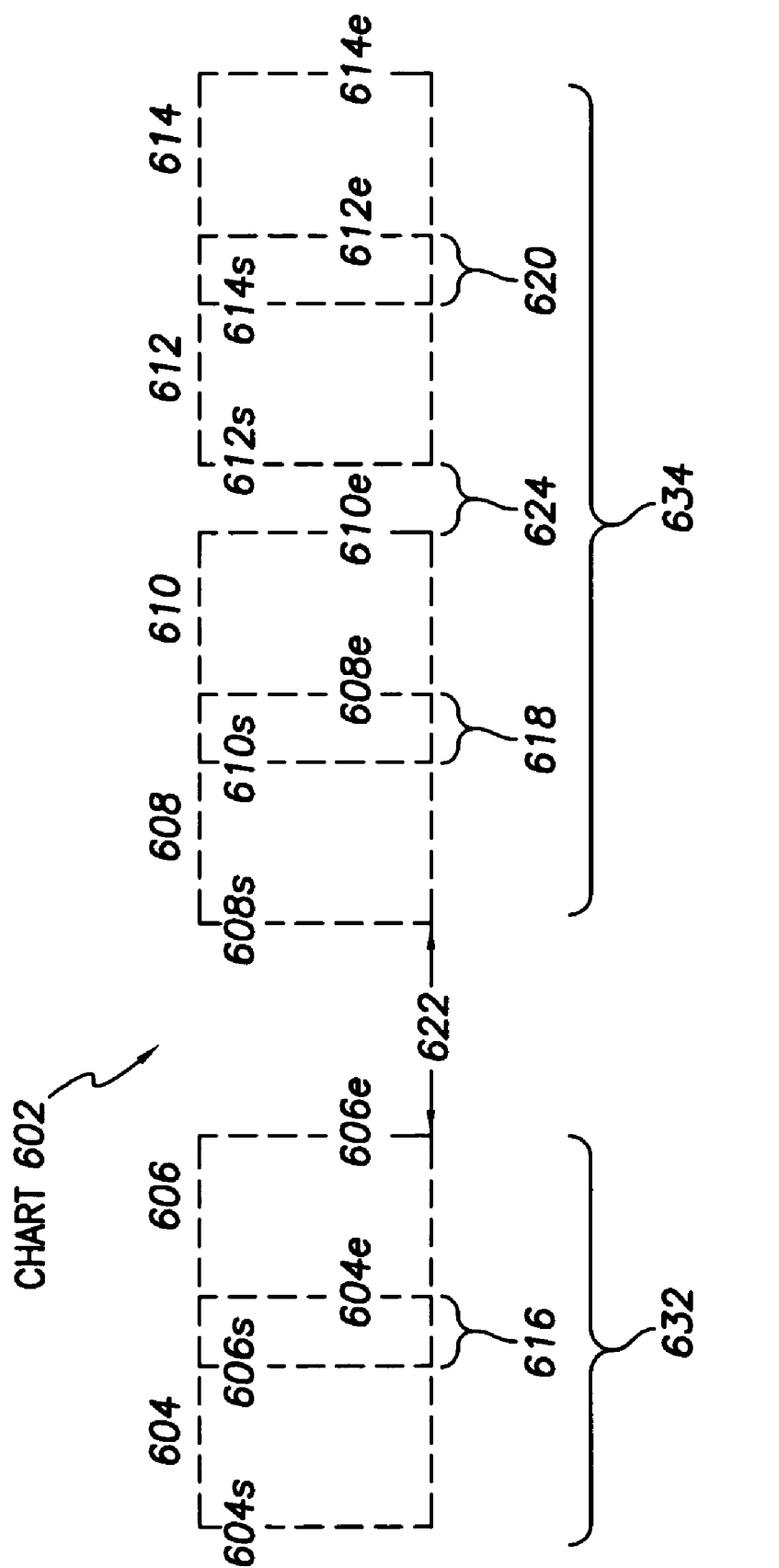
FIG. 6 illustrates a graphical representation of data ranges which are evaluated to formulate a data request in accordance with one exemplary technique.

FIG. 6 illustrates another example of formulating efficient IMD data transfer requests such as read commands. FIG. 6 illustrates a graphical chart 602 of sorted data ranges calculated from a set of target event addresses. Chart 602 is similar to chart 514 described above in relation to FIG. 5. In this example, chart 602 includes six data range address 604-614. Consistent with FIG. 5, a starting and ending point of each data range is indicated with the suffixes 's' and 'e' respectively. In FIG. 6, data ranges 604 and 606 overlap as is indicated at 616. Similarly, data ranges 608 and 610 overlap as indicated at 618 and data ranges 612 and 614 overlap as indicated at 620.

Further, in this example, there are two instances where the data ranges do not overlap. One such instance is indicated at 622 between data ranges 606 and 608. The other instance of non-overlap is between data ranges 610 and 612, as indicated at 624. In instances where data ranges do not overlap, exemplary techniques can be employed to determine if a data request should be formulated which encompasses the adjacent but non-overlapping data ranges. For instance, as mentioned above, sending a data request uses a determinable amount of processing and data transmission resources. In some instances, a single data request encompassing an amount of unneeded data which separates two adjacent data ranges may utilize less resources than two separate data requests for the individual data ranges. An amount or value can be predefined which accounts for the processing and data transmission resources utilized for each additional data request.

In relation to the illustrated example of FIG. 6, assume that predefined amount is, for instance, 4 bytes. So, for example, a gap between adjacent data ranges of 4 bytes or greater results in separate data requests being formulated for the adjacent data ranges and a gap of less than 4 bytes results in a single data request being formulated which encompasses the adjacent data ranges. Assume further, that in the illustrated example of chart 602, that gap 622 is greater than 4 bytes and that gap 624 is less than 4 bytes. In this scenario, a first data request 632 is formulated to encompass data ranges 604 and 606, while a second data request 634 is formulated to encompass data ranges 608-614. Such a technique efficiently utilizes data transmission resources to the patient's benefit.

CONCLUSION

The foregoing discussion describes techniques for efficient data transfer involving an IMD. Although the inventive principles have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A system comprising:
an implantable medical device (IMD) having memory and configured to record into memory patient data including at least first and second target events; and,
a computing system separate from the IMD, configured to communicate with the IMD to retrieve patient data including the first and second target events using a single data request command, the computing system comprising:
a range calculation module configured to determine a first data address range in IMD memory encompassing the first target event and a second data address range in IMD memory encompassing the second target event;
a range overlap detection module configured to detect whether the first and second data address ranges in IMD memory overlap;
a data request formulation module configured to, in response to an instance where the first and second data address ranges in IMD memory overlap, formulate the single data request command for the IMD, wherein the command includes a request for patient data stored within the overlapping data address ranges in IMD memory; and
a transceiver for transmitting the single command to the IMD and receiving from the IMD patient data stored in IMD memory.

2. The system according to claim 1, wherein the IMD comprises an IMD configured to record cardiac electrogram data and to identify target events within the electrogram data.

3. The system according to claim 1, wherein the computing system comprises a programmer, and wherein the range calculation module, range overlap detection module, and the data request formulation module are embodied on the programmer.

4. The system of claim 1, wherein the at least first and second target events are embodied as target event addresses which represent a stored location of target event data buffered in memory of the IMD.

5. The system of claim 1, wherein the at least first and second target events are target events relating to at least one of neural activity, impedance, intrinsic heart rate, heart rate recovery, heart rate variability, conduction delay, pressure, posture, and activity.

6. The system of claim 1, wherein the at least first and second target events are target events relate to a single measured parameter.

7. The system of claim 1, wherein the range overlap detection module is configured to sort the first and second data ranges according to an order in which the corresponding first and second target events are stored.

8. The system of claim 1, wherein the data request formulation module is further configured to, in an instance where no overlap is detected between the two data ranges but where an amount of data between the two data ranges is less than a predefined value, formulate a single data request which encompasses two data ranges.

9. A system comprising:
- implantable means for recording into its memory a set of target events relating to patient data sensed by the implantable means; and
- computing means separate from the implantable means and comprising
  - means for obtaining the set of target events;
  - means for calculating data ranges in memory of the implantable means associated with individual target events of the set;
  - means for sorting the data ranges of the set;
  - means for detecting overlapping portions of the data ranges of the set; and
  - means for, in response to detecting overlapping portions of data ranges, formulating a data request for transmission to the implantable means, which includes at least portions of at least two data ranges having overlapping portions.

10. The system of claim 9, wherein means for sorting comprises means for sorting the data ranges by chronological order.

11. The system of claim 9, wherein means for detecting comprises means for detecting an incidence where a start time of a first data range falls between a start time and an end time of a second data range.

12. The system of claim 9, wherein means for formulating comprises means for formulating the data request specifying a starting buffer address of the memory of the implantable means and an ending buffer address of the memory of the implantable means.

13. The system of claim 9 further comprising means for formulating the data request to encompass at least two data ranges which are separated by a time duration which is less than a predefined value.

* * * * *